(12) United States Patent
Schäller et al.

(10) Patent No.: US 8,979,845 B2
(45) Date of Patent: Mar. 17, 2015

(54) ELECTROSURGICAL FORCEPS

(75) Inventors: Daniel Schäller, Tuebingen (DE); Klaus Fischer, Nagold (DE); Dieter Hafner, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 445 days.

(21) Appl. No.: 13/391,105

(22) PCT Filed: Aug. 11, 2010

(86) PCT No.: PCT/EP2010/004924
§ 371 (c)(1),
(2), (4) Date: Mar. 5, 2012

(87) PCT Pub. No.: WO2011/020578
PCT Pub. Date: Feb. 24, 2011

(65) Prior Publication Data
US 2013/0079764 A1  Mar. 28, 2013

(30) Foreign Application Priority Data

Aug. 20, 2009 (DE) .......................... 10 2009 038 171
Oct. 14, 2009 (DE) .......................... 10 2009 049 401

(51) Int. Cl.
*A61B 18/18* (2006.01)
*A61B 18/14* (2006.01)

(52) U.S. Cl.
CPC .............. *A61B 18/18* (2013.01); *A61B 18/1442* (2013.01); *A61B 2018/1412* (2013.01); *A61B 2018/1455* (2013.01)
USPC .................................. 606/51; 606/50; 606/49

(58) Field of Classification Search
CPC .................. A61B 18/1445; A61B 2018/0063; A61B 18/1442; A61B 2018/1455; A61B 2018/00601; A61B 2018/1412
See application file for complete search history.

(56) References Cited

U.S. PATENT DOCUMENTS

| 2,031,682 A | 2/1936 | Wappler et al. |
| 6,676,660 B2 | 1/2004 | Wampler et al. |

(Continued)

FOREIGN PATENT DOCUMENTS

| CN | 1608597 | 4/2005 |
| CN | 201529148 | 7/2010 |

(Continued)

OTHER PUBLICATIONS

Russian Office Action Dated Oct. 3, 2013, English translation attached to original, All together 6 Pages.

(Continued)

*Primary Examiner* — Christopher D Koharski
*Assistant Examiner* — Philip Edwards
(74) *Attorney, Agent, or Firm* — Brooks Kushman P.C.

(57) ABSTRACT

Electrosurgical forceps for efficiently severing of hollow organs, in particular vessels. The electrosurgical forceps have a first branch and a second branch for gripping the hollow organ. The forceps have at least one neutral electrode on the second branch, at least one first coagulation electrode and a second coagulation electrode that is disposed on the first branch for applying a first HF current by means of the coagulation electrode, and at least one cutting device, which is arranged between the coagulation electrodes in order to sever the hollow organ in a cutting region. The cutting device has a cutting electrode for applying a second HF current between the cutting and neutral electrodes. The coagulation electrodes are arranged spaced apart from one another in such a way that the first HF current does not flow through or only a minor amount of the same flows through the cutting region.

7 Claims, 2 Drawing Sheets

(56) References Cited

U.S. PATENT DOCUMENTS

| | | | |
|---|---|---|---|
| 7,033,356 | B2 | 4/2006 | Latterell et al. |
| 7,717,915 | B2 | 5/2010 | Miyazawa |
| 7,850,688 | B2 | 12/2010 | Hafner |
| 2005/0159745 | A1 | 7/2005 | Truckai et al. |
| 2005/0171535 | A1* | 8/2005 | Truckai et al. .......... 606/48 |
| 2007/0233060 | A1 | 10/2007 | Hafner |

FOREIGN PATENT DOCUMENTS

| | | |
|---|---|---|
| DE | 4421822 C1 | 10/1995 |
| DE | 102004055671 | 2/2006 |
| JP | 2002095676 | 4/2002 |
| JP | 2003245285 | 9/2003 |
| JP | 2007050181 | 3/2007 |
| JP | 2008055167 | 3/2008 |
| WO | 02058542 | 8/2002 |
| WO | 02058542 A2 | 8/2002 |
| WO | 02058542 A3 | 8/2002 |

OTHER PUBLICATIONS

International Search Report for PCT/EP2010/004924, English translation attached to original, Both completed by the European Patent Office on Oct. 21, 2010, All together 5 Pages.

International Preliminary Report on Patentability and Written Opinion, Issued by the International Bureau of WIPO on Feb. 21, 2012, All together 5 Pages.

Office Action for JP 2012-525076, English Summary attached to original, Dated Sep. 17, 2013, All together 5 Pages.

Chinese Office Action for CN 201080036943.X, English Translation attached to original, Issue Date of Nov. 29, 2013, All together 13 Pages.

* cited by examiner

ELECTROSURGICAL FORCEPS

CROSS-REFERENCE TO RELATED APPLICATION

This application is the U.S. national phase of PCT Appln. No. PCT/EP2010/004924 filed Aug. 11, 2010 which claims priority to German application DE 10 2009 038 171.6 filed Aug. 20, 2009 and German application DE 10 2009 049 401.4 filed Oct. 14, 2009, the disclosures of which are incorporated in their entirety by reference herein.

The invention relates to an electrosurgical forceps as per the preamble of claim 1.

For many years now, electrosurgical instruments have been used in electrosurgery (RF surgery) for coagulating biological tissue or else for cutting the latter. During coagulation, radiofrequency current is routed through the tissue to be treated so that the latter changes as a result of protein coagulation and dehydration. In the process, the tissue contracts in such a way that the vessels are closed-off and bleeding is suppressed. After the successful coagulation, the tissue can be completely severed while avoiding strong bleeding.

DE 44 218 22 has disclosed a corresponding endoscopic, bipolar RF coagulation instrument with an integrated cutting apparatus. This is an endoscopic forceps consisting of two branches that are hinged with respect to one another. The branches have jaw parts for gripping tissue. Each of these jaw parts respectively has one pair of electrodes, which extend on alternate sides along the longitudinal axis of the jaw parts. In the closed state, the pairs of electrodes are situated opposite one another. It is possible to grip tissue by means of the jaw parts and then to apply an RF current such that the tissue between these pairs of electrodes is coagulated. DE 44 218 22 has a mechanical cutting device arranged centrally between the pairs of electrodes. The cutting device comprises a knife that can be displaced along the longitudinal axis of the jaw parts after gripping and coagulating the tissue. Hence this knife serves to sever the coagulated tissue.

The cuts produced by this RF coagulation instrument are not always satisfactory. Moreover, it is difficult to operate the cutting device.

Proceeding from DE 44 218 22, it is an object of the present invention to provide an improved electrosurgical forceps.

This object is achieved by an instrument as per the present claim 1.

In particular, in the case of an electrosurgical forceps or an electrosurgical instrument with a first branch and a second branch for gripping a hollow organ, comprising at least one neutral electrode on the second branch;

at least one first coagulation electrode and a second coagulation electrode, which is arranged on the first branch for applying a first RF current by means of the coagulation electrodes and the neutral electrode for the purpose of at least partly closing-off the hollow organ; and at least one cutting device, arranged between the coagulation electrodes for severing the at least partly closed-off hollow organ in a cutting region, the object is achieved by virtue of the fact that the cutting device comprises at least one cutting electrode for applying a second RF current by means of the cutting electrode and the neutral electrode, the coagulation electrodes being arranged at a distance from one another such that the first RF current does not flow, or hardly flows, through the cutting region.

Thus, an idea of the present invention consists of providing an electrosurgical cutting device in place of the mechanical cutting device. The cutting electrode serves this purpose and, while using the neutral electrode, applies a second RF current that is designed such that the gripped tissue or the gripped hollow organ is severed. This approach is problematic because the tissue is dried out during the preceding coagulation using the first RF current. In order to ensure a clean cut by means of the second RF current, the present invention proposes to design and align the coagulation electrodes such that there is no coagulation in the cutting region, i.e. the region of the hollow organ that should be severed. Thus, the intent is to prevent the tissue in the cutting region from drying out such that there is sufficiently preserved tissue during the cutting process, which can be severed quickly and efficiently by means of the second RF current.

The coagulation electrodes are preferably arranged at such a distance from one another that no RF current flows through the cutting region during a coagulation phase—i.e. while the hollow organ is at least partly closed-off. At the very least, the coagulation electrodes should be arranged at such a distance from one another that the current flow can be kept so low in the cutting region, even over a relatively long period of time, that there is no disadvantageous tissue change, more particularly disadvantageous for a cut.

The electrosurgical forceps can have at least one recess for holding the cutting region when gripping the hollow organ. The recess ensures that there is no or only little damage to the cutting region when the tissue is gripped. This is how, according to the invention, mechanical damage to the cutting region should be avoided before the final severing. Mechanical damage of the tissue can also be bothersome during an electrosurgical severance procedure.

The electrosurgical forceps can comprise at least a first and a second neutral electrode, which are insulated from one another at least in sections and respectively arranged corresponding to the first and the second coagulation electrode. This renders it possible to provide an appropriately corresponding neutral electrode for each coagulation electrode. This pair-wise arrangement of the first neutral electrode and the first coagulation electrode, and the second neutral electrode and the second coagulation electrode, renders it possible to route the current path of the first RF current such that damage to the tissue in the cutting region is avoided.

The neutral electrodes are preferably arranged directly adjacent to the coagulation electrodes. That is to say the electrodes are arranged opposite one another in the closed state of the forceps.

The first and the second neutral electrode can have a substantially planar design and span a plane. The neutral electrodes are preferably arranged such that the planes intersect at an angle, more particularly at an acute angle. The angle at which the planes of the neutral electrodes intersect should be less than 150 degrees, more particularly less than 130 degrees, more particularly less than 110 degrees, more particularly less than or equal to 80 degrees. As a result of the tilted arrangement of the neutral electrode with respect to the fixation plane of the hollow organ, the neutral electrode acts as an electrode with a very small area. There is a high current influx during coagulation, during which a spatially very restricted region of the organ is coagulated. This is advantageous for the cutting procedure by means of the cutting device.

The coagulation electrodes can likewise have such a planar design that these also span a plane. The coagulation electrodes should also be arranged such that the planes of the coagulation electrodes intersect at an angle. This cutting angle should also be less than 150 degrees, more particularly less than 130 degrees, more particularly less than 110 degrees, more particularly less than or equal to 80 degrees. In one exemplary embodiment, this angle can be an acute angle.

Hence, the coagulation electrodes can also be arranged such that the effective area of the electrodes is significantly smaller than their actual area. This allows quick and efficient coagulation. It is preferable for the first neutral electrode to be arranged parallel to the first coagulation electrode and for the second neutral electrode to be arranged parallel to the second neutral electrode such that the tissue is coagulated in an optimal fashion. By tilting the respective electrode pair there is a particularly advantageous coagulation procedure when closing the branches and hence when gripping the tissue.

The coagulation electrodes can have a small coagulation electrode width, more particularly of less than or equal to 3 mm or of less than or equal to 2 mm. The coagulation electrodes preferably extend along the longitudinal axis of the electrosurgical forceps, with the width of said coagulation electrodes being relatively small compared to their length. The RF energy applied through electrodes which are this narrow is concentrated on a relatively narrow section of the hollow organ. Thus, a successful coagulation can already be achieved after a very short application time, with the coagulation edge expanding minimally. As a result, the tissue in the cutting region or in the center of the forceps has sufficient moistness and is sufficiently conductive to be quickly and efficiently severed by means of the second RF current.

The first and the second branch can respectively comprise a jaw part for gripping the organ, the jaw parts being designed such that they contact one another in a contact region when the forceps is in a closed state. This contact region is preferably provided with one or more insulators for electric insulation of the coagulation electrodes from the neutral electrode, even in the closed state of the forceps. This can prevent short circuits that could have a damaging effect on the utilized RF generator.

Further advantageous embodiments emerge from the dependent claims.

In the following text, the invention will be described by means of a number of exemplary embodiments, which should be explained in more detail on the basis of the figures. In this context:

In the following description, the same reference signs are used for identical parts and parts with an identical effect.

Figure 1:
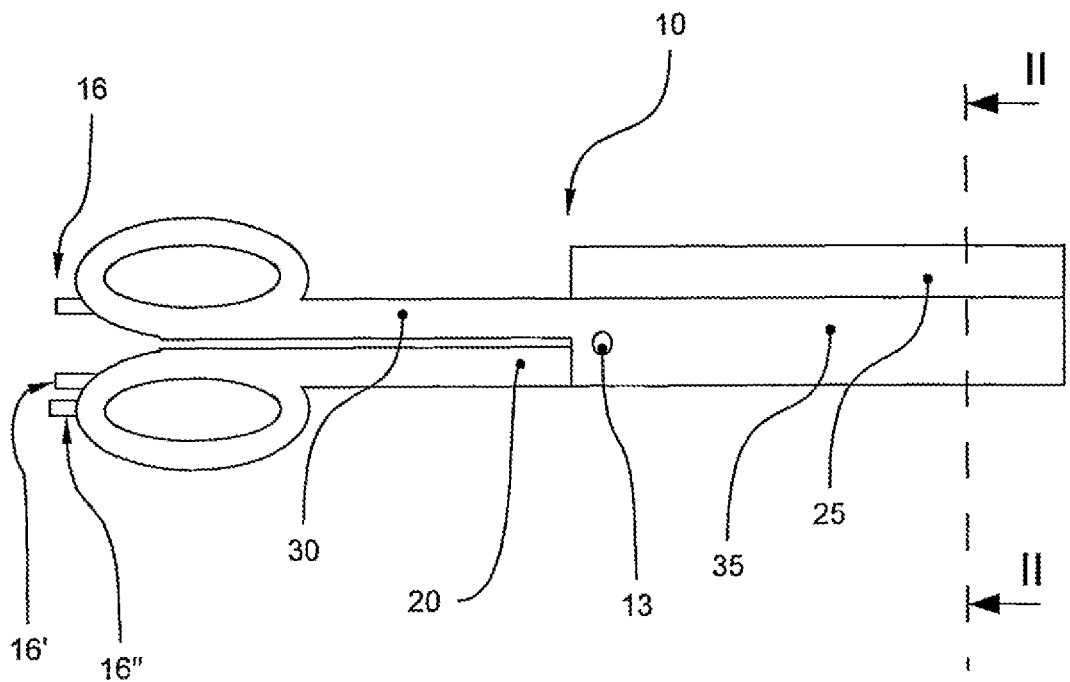
FIG. 1 shows an electrosurgical forceps.

FIG. 1 shows a schematic illustration of an electrosurgical forceps 10, which consists of a first branch 20 and a second branch 30. The individual branches 20, 30 are interconnected in a rotary fashion by means of a pivot joint 13. At the proximal end of the branches 20, 30, there respectively are grips for operating the forceps 10. The proximal ends have RF connectors 16, 16', 16" for connecting the electrosurgical instrument, i.e. the forceps 10, to an RF generator. The distal end of the electrosurgical forceps 10 has a first jaw part 25 (part of the first branch 20) and a second jaw part 35 (part of the second branch 30).

Figure 2:
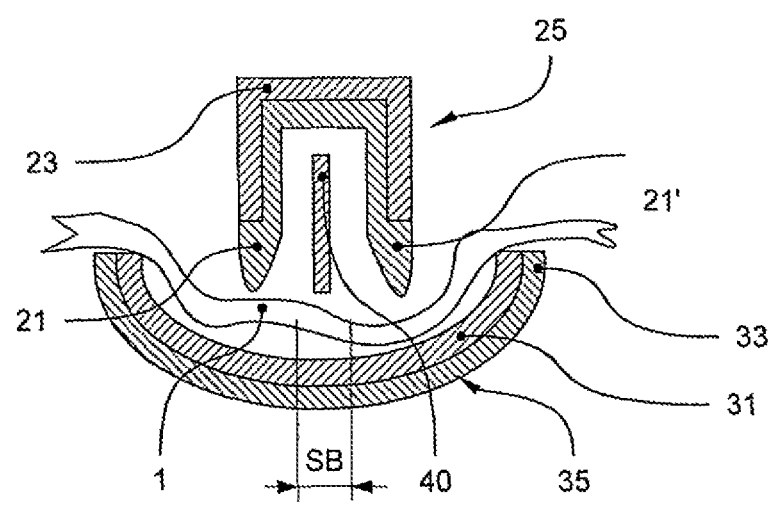
FIG. 2 shows a first exemplary embodiment of the jaw parts of the electrosurgical forceps from FIG. 1.

FIG. 2 shows a section through these jaw parts 25, 35. In a closed state of the forceps 10, the second jaw part 35 grips around the first jaw part 25 at least in sections. A hollow organ, e.g. a vessel 1, can be fixed between the first jaw part 25 and the second jaw part in this closed state. In the exemplary embodiment shown in FIG. 2, the second jaw part 35 in cross section has the design of a rounded U-profile. It has a frame 33, which consists of an electrically non-conductive material. The entire inner face of the frame of the second jaw part 35 has been coated with a neutral electrode 31, which is designed for the application of an RF current. The first jaw part 25 is embodied as an inverted U-profile, and likewise has an electrically non-conductive frame 23, the inner face of which has been coated with an electrically conductive material. The electrically conductive material projects beyond the frame 23 in the direction of the second jaw part 35. These protruding sections form a first and a second coagulation electrode 21, 21'. In the closed state of the forceps 10, the vessel 1 is clamped between the first coagulation electrode 21 and the neutral electrode 31 and between the second coagulation electrode 21' and the neutral electrode 31. A first RF current can be applied during a coagulation phase for closing-off the vessel 1. The corresponding RF voltage is applied between the coagulation electrodes 21, 21' and the neutral electrode 31. In order to avoid a potential difference between the coagulation electrodes 21, 21', these are electrically interconnected. The two coagulation electrodes 21, 21' are together connected to the RF generator via the RF connector 16'.

In cross section, the coagulation electrodes 21, 21' are spaced apart from one another such that this results in a holding region or a recess centrally between said electrodes. The vessel 1 below the recess is not contacted by the first jaw part 25, even in the closed state of the forceps 10. An electric knife 40 can be guided along the longitudinal direction of the first jaw part 25 in this region in order to sever the vessel 1 after the coagulation phase. To this end, an RF voltage is applied between the electric knife 40 and the neutral electrode 31. The applied second RF current severs the vessel 1 in a cutting region SB (cutting phase).

Although the coagulation/cutting procedure was described as a sequential process in the preceding exemplary embodiment, it is possible to carry out the coagulation and cutting phases at the same time, or at least with a partial time overlap.

Figure 3:
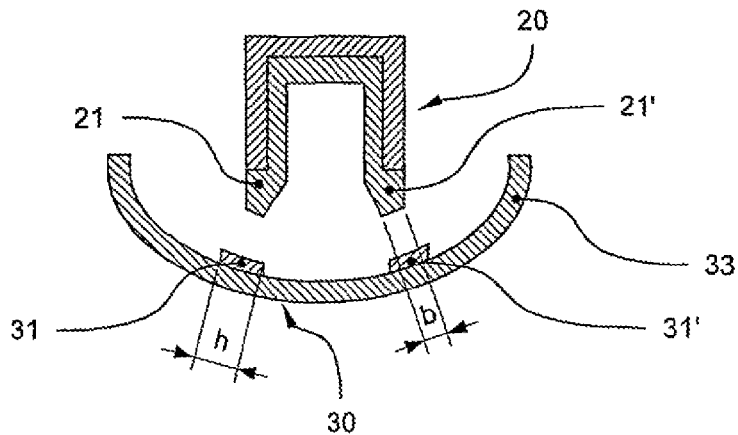
FIGS. 3 to 6 show further embodiments of jaw parts according to the invention.

FIG. 3 shows a further exemplary embodiment of the forceps 10 according to the invention, the jaw parts 25, 35 likewise being embodied as U-profiles or as inverted U profile. However, compared to the ends of the coagulation electrodes 21, 21' in FIG. 2, these have a flattened design (convex in the former). Moreover, the second jaw part 35 does not have just one large-area neutral electrode 31, but two neutral electrodes 31, 31' that are arranged in a spatially separate manner. These flattened ends of the first jaw part 25 run substantially parallel to the two neutral electrodes 31, 31', which are arranged on the frame 33 of the second brand 30. The coagulation electrodes 21, 21' have a defined coagulation electrode width b, which lie on the first neutral electrode 31 or on the second neutral electrode 31' with the neutral electrode width h, in the closed state of the forceps 10. According to the invention, the coagulation electrode widths b and the neutral electrode widths h should have a relatively small embodiment such that there is a high RF current influx in a spatially restricted area of the vessel 1. Hence, this can prevent the vessel 1 from drying out in the cutting region SB.

The coagulation electrodes 21, 21' as per the exemplary embodiment in FIG. 3 are slightly tilted with respect to the horizontal. This results in a substantially smaller effective area when the forceps 10 is closed, during which the vessel 1 only partly contacts the coagulation electrodes 21, 21'. As illustrated in FIG. 3, the neutral electrodes 31, 31' preferably also have a corresponding tilt.

Figure 4:
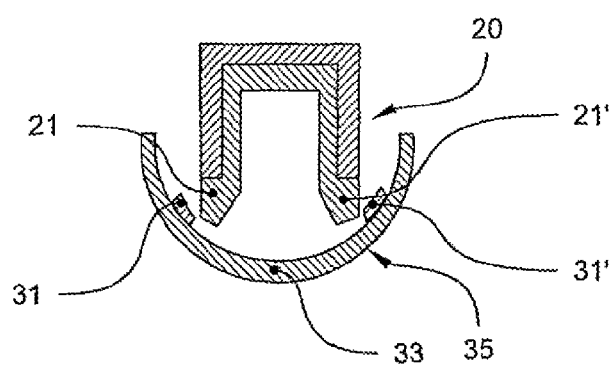

In the exemplary embodiment as per FIG. 4, the neutral electrodes 31, 31' are not arranged below the coagulation electrodes 21, 21' but next to them. The coagulation electrodes 21, 21' directly contact the frame 33 of the second jaw part 35 in the closed state. No contact is made between the neutral electrodes 31, 31' and the coagulation electrodes 21, 21'. The neutral electrodes 31, 31' are arranged on the frame 33 of the second jaw part 35 such that the coagulation electrodes 21, 21' come to rest next to these in the closed state of the forceps 10. As soon as tissue is clamped, this results in a shortest current path from the lateral regions of the coagulation electrodes 21, 21' to the neutral electrodes 31, 31'. While the cutting region SB is situated between the coagulation electrodes 21, 21', the neutral electrodes are arranged on alternate sides outside of the region covered by the second jaw part 35. Hence the cutting region SB is electrically shielded by the second jaw part 35, more particularly by the coagulation electrodes 21, 21' arranged thereon. Action of the first RF current on the cutting region SB clasped by the second jaw part 35 is very unlikely.

Figure 5:
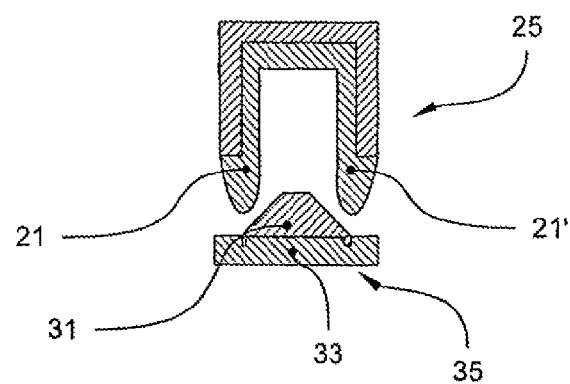

In a further embodiment of the invention, the neutral electrode 31 is arranged centrally between the coagulation electrodes 21, 21' (see FIG. 5). The neutral electrode 31 forms a web, which extends along the longitudinal direction of the second jaw part 35 and is encompassed by the first jaw part 25 in the closed state.

In the closed state of the forceps 10, there are also laterally arranged effective areas of the neutral electrode 31 in the exemplary embodiment as per FIG. 5. Hence, a vessel 1 possibly lying on the web in the cutting region SB is not damaged by the first RF current because there are significantly shorter current paths available which run horizontally. The web in the exemplary embodiment as per FIG. 5 is arranged in an areal fashion on a substantially planar frame 33 of the second jaw part 35.

Figure 6:
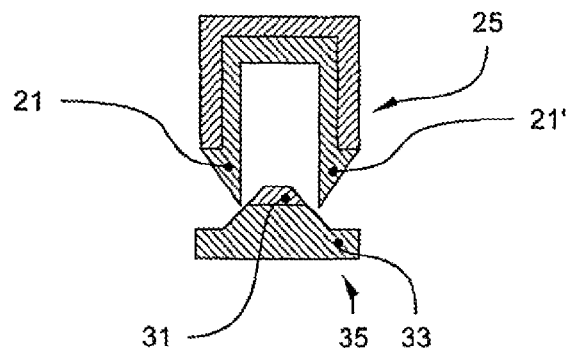

By contrast, in the exemplary embodiment as per FIG. 6, the frame 33 already forms part of the web extending along the longitudinal direction of the second jaw part 35. Only an upper section of the web is provided with the neutral electrode 31. Thus, the neutral electrode is arranged such that there is no direct contact between the coagulation electrodes 21, 21' and the neutral electrode 31 in the closed state of the forceps 10. The contact can only be established over the tissue. Thus, a short circuit between the electrodes 21, 21', 31 is prevented. In the closed state, a portion of the coagulation electrodes 21, 21' lies on the frame 33 of the second jaw part 35. Hence the whole contact region on the side of the second jaw part 35 is embodied as electrical insulator.

LIST OF REFERENCE SIGNS

1 Vessel
10 Electrosurgical forceps
13 Pivot joint
16, 16', 16" RF connector
20 First branch
21, 21' Coagulation electrode
23 Frame
25 First jaw part
30 Second branch
31, 31' Neutral electrode
33 Frame
35 Second jaw part
40 Electric knife
b Coagulation electrode width
h Neutral electrode width
SB Cutting region

The invention claimed is:

1. An electrosurgical forceps with a first branch and a second branch for gripping a hollow organ, comprising:
at least one first neutral electrode and a second neutral electrode on the second branch, the first and second neutral electrodes being characterized in that the first and the second neutral electrodes respectively span a plane and are arranged such that the planes intersect at an acute angle;
at least one first coagulation electrode and a second coagulation electrode respectively arranged corresponding to the first and the second neutral electrodes for applying a first RF current by means of the coagulation electrodes and the neutral electrode;
at least one cutting device, arranged between the coagulation electrodes for severing the hollow organ in a cutting region,
characterized in that
the cutting device comprises at least one cutting electrode for applying a second RF current by means of the cutting electrode and the neutral electrode, the coagulation electrodes being arranged at a distance from one another such that the first RF current does not flow, or hardly flows, through the cutting region when it is applied.

2. The electrosurgical forceps as claimed in claim 1, characterized by at least one recess for holding the cutting region when gripping the hollow organ.

3. The electrosurgical forceps as claimed in claim 1 wherein the first and second neutral electrodes are electrically insulated from one another at least in sections.

4. The electrosurgical forceps as claimed in claim 1, characterized in that the coagulation electrodes respectively span a plane and are arranged such that the planes intersect at an angle, more particularly at an acute angle.

5. The electrosurgical forceps as claimed in claim 1, characterized in that the coagulation electrodes have a small coagulation electrode width, more particularly of less than or equal to 3 millimeters or of less than or equal to 2 millimeters.

6. The electrosurgical forceps as claimed in claim 1, characterized in that the first and the second branch comprise jaw parts that are designed such that they contact one another in a contact region when the forceps is in a closed state, the contact region comprising an insulator for electric insulation of the coagulation electrodes from the at least one neutral electrode in the closed state.

7. An electrosurgical forceps with a first branch and a second branch for gripping a hollow organ, the forceps comprising:
at least one neutral electrode on the second branch, wherein at least parts of the second branch are embodied as a U-profile, wherein the inner face of the U-profile includes the at least one neutral electrode;
at least one first coagulation electrode and a second coagulation electrode which is arranged on the first branch for applying a first RF current by means of the coagulation electrodes and the neutral electrode, wherein at least parts of the first branch are embodied as an inverted U-profile wherein the inverted U-profile and the U-profile are arranged such that in a closed state of the forceps tissue is clamped between the first coagulation electrode and the neutral electrode and between the second coagulation electrode and the neutral electrode; and
at least one cutting device arranged between the coagulation electrodes for severing the hollow organ in a cutting region, wherein the cutting device includes at least one cutting electrode for applying a second RF current by means of the cutting electrode and the neutral electrode and the coagulation electrodes are arranged at a distance from one another on the inverted U-profile such that the first RF current does not flow, or hardly flows, through the cutting region when it is applied.

* * * * *